United States Patent [19]

Ward

[11] Patent Number: 4,950,685
[45] Date of Patent: Aug. 21, 1990

[54] WOOD PRESERVATIVES
[75] Inventor: Hans A. Ward, New Kensington, Pa.
[73] Assignee: Kop-Coat, Inc., Pittsburgh, Pa.
[21] Appl. No.: 397,692
[22] Filed: Aug. 23, 1989

Related U.S. Application Data

[63] Continuation-in-part of Ser. No. 286,971, Dec. 20, 1988, abandoned, which is a continuation of Ser. No. 890,015, Jul. 28, 1986, abandoned, which is a continuation-in-part of Ser. No. 700,031, Feb. 11, 1985, abandoned.

[51] Int. Cl.$^5$ .................... A01N 47/10; A01N 33/12
[52] U.S. Cl. ................................ 514/479; 514/642; 514/643
[58] Field of Search .................... 514/479, 642, 643

[56] References Cited
FOREIGN PATENT DOCUMENTS
1462043 1/1977 United Kingdom .

OTHER PUBLICATIONS
Chemical Abstracts, vol. 87, No. 87:103500p—Butcher et al (1977).
Chemical Abstracts, vol. 92, No. 92:75897f—Singer (1980).
Chemical Abstracts; vol. 93 (1980); #180811s; Hulme et al.
Chemical Abstracts; vol. 82 (1975); #81688y; Bent et al.

*Primary Examiner*—Joseph A. Lipovsky
*Attorney, Agent, or Firm*—Arnold B. Silverman

[57] ABSTRACT

A synergistic wood preservative composition is provided comprising a quaternary ammonium compound and 3-iodo-2-propynyl butyl carbamate having the properties of providing stain resistance to wood. The quaternary ammonium compound is preferably selected from the group consisting of didecyldimethyl ammonium chloride, tri-methyl-coco-ammonium chloride and dimethyl-di-coco-ammonium chloride.

8 Claims, No Drawings

WOOD PRESERVATIVES

This application is a Continuation-In-Part of Ser. No. 07/286,971 filed Dec. 20, 1988, now abandoned, which was a continuation of Ser. No. 06/890,015 filed Jul. 28, 1986, abandoned, which in turn was a continuation in part of Ser. No. 06/700,031 filed Feb. 11, 1985, now abandoned.

BACKGROUND OF THE INVENTION

Wood is one of the best structural materials for the construction of buildings because of its strength, ease of processing, and relatively low cost. Wood, however, has one serious drawback in that it is susceptible to decay by wood destroying fungi and attacked by woodworms, borers and termites. Wood is also cosmetically damaged by molds, mildews and stain fungi. To eliminate structural damage caused by fungi, wood-worms, borers and termites, wood is traditionally treated with preservatives such as CCA (copper-chromium-arsenic solutions), pentachlorophenol, creosote oil and the like by pressure impregnation. To eliminate cosmetic damage, wood is traditionally immersed in solutions containing salts of chlorinated phenols. In recent years there has been a demand for wood preservatives which do not discolor wood like CCA or creosote and do not contain chlorinated phenols because of suspected human safety problems.

Wood preservative compositions comprising didecyl-dimethyl ammonium chloride as the active ingredient are known to be effective against wood damaging fungi and termites. See generally, *Chemical Abstracts*, Vol. 87, No.87:103500p, Butcher et al. (1987). Wood preservative compositions comprising 3-iodo-2-propynyl butyl carbamate as the active ingredient are known to be effective against fungi that cause structural and cosmetic damage to wood. See generally, *Chemical Abstracts*, Vol. 92, No. 92:75897f, Singer (1980). This invention is directed to synergistic combinations of these two preservatives.

BRIEF DESCRIPTION OF THE INVENTION

This invention relates to wood preservative compositions effective in treating fungi which cause stain, while providing effective protection against brown and white rot, mildew, soft rot and mold. More particularly, this invention relates to wood preservative compositions comprising a synergistic combination of didecyl-dimethyl ammonium chloride (alternatively referred to as DDAC) which has the structural formula:

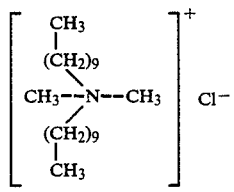

and 3-iodo-2-propynyl butyl carbamate (alternatively referred to as IPBC) which has the structural formula:

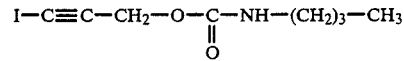

The invention also contemplates the use of tri-methyl-coco-ammonium chloride or dimethyl-di-cocoammonium chloride in lieu of DDAC.

DETAILED DESCRIPTION OF THE INVENTION

The preservative compositions of the invention can be prepared as solutions or emulsions by conventional means using water or organic solvents or simply mixed together as DDAC.

A preferred form is to combine a water solution of DDAC with an organic solvent solution of IPBC to create an emulsion. DDAC acts as a surfactant to emulsify the IPBC solution. The resulting emulsion is diluted with water and can be applied to wood by conventional treating methods such as immersion, brush, spray or pressure.

The quantity and ratio of DDAC to IPBC will depend upon the specific application. Generally, however, the preservative composition will contain from about 1 to 80 parts by weight DDAC per about 1 to 10 parts by weight IPBC A preferred ratio of DDAC to IPBC is from 4:1 to 20:1 parts by weight, i.e., about 4 to 20 parts by weight DDAC to per parts by weight IPBC. The solvent will generally consist of from 90 to 99 percent by weight of the total wood preservative composition ready for use. Typical solvents include combinations of water, aromatic solvents, polar solvents and aliphatic solvents. It may be advantageous to supply the preservative composition in concentrated form with about 20 to 40 percent by weight solvent with the remaining solvent being added prior to use.

If desired, the wood preservative composition may incorporate other preservatives. Typical preservatives include pentachlorophenol, zinc naphthenate, copper naphthenate and the like.

The following examples will serve to illustrate the invention and preferred embodiments thereof All parts and percentages in said examples and elsewhere in the specification and claims are by weight unless otherwise indicated.

EXAMPLE 1

Ten red pine samples (10×10×100 mm) were immersed in each preservative composition, listed in Table 1, for five minutes. DDAC was obtained from Lonza, Inc. of Fair Lawn, New Jersey as a water solution under the trade name Bardac 2280. IPBC was obtained from Troy Chemical Corporation of Newark, New Jersey as a solvent solution under the trade name Troysan Polyphase AF-1. To prepare the solutions shown in Table 1, proportions of Bardac 2280 and Troysan Polyphase AF-1 were mixed together and diluted with ethanol to provide the concentration of active ingredient shown.

As an example, to prepare composition 1 in Table 1, the following formula was used:

| Ingredient | % by weight |
| --- | --- |
| Troysan Polyphase AF-1 | .6250 |
| Bardac 2280 | .3125 |
| Ethanol | 99.0625 |

-continued

| Ingredient | % by weight |
|---|---|
| | 100.0000 |

The components of Bardac 2280 as obtained from its manufacturer are as follows:

| Component | % by weight |
|---|---|
| Didecyldimethyl ammonium chloride | 80.0 |
| Ethanol | 10.0 |
| Water | 10.0 |
| | 100.0 |

The components of Troysan Polyphase AF-1 as obtained from its manufacturer are as follows:

| Component | % by weight |
|---|---|
| 3-Iodo-2-propynyl butyl carbamate | 40.0 |
| Hiflash aromatic naptha | 25.0 |
| Dipropylene Glycol | 15.0 |
| Dimethyl sulfoxide | 15.0 |
| C-8, C-10 aliphatic glycidyl ethers | 5.0 |
| | 100.0 |

Where Bardac 2280 or Troysan Polyphase AF-1 were used alone they were diluted with ethanol. The treated samples were mixed randomly and exposed in dishes to the following three groups of wood damaging fungi. The fungi used were:

| GROUP #1 | |
|---|---|
| Molds | Mildew |
| Aspergillus niger | Aureobasidium |
| Paecilomyces varioti | pullalaria |
| Trichoderma viride | Hormiscium sp. |
| Gliocladium sp. | Torula sp. |
| Stain | |
| Chlorociboria aeruginascens | |
| Cerotocystis vescus | |
| Diplodia gossypina | |
| GROUP #2 | |
| Brown Rot | White Rot |
| Gloephyllum trabeum | Trametes versicolor |
| Lentinus lepideus | Trametes sp. |
| Poria placenta | Polyporus sp. |

Serpula lacrimans

| GROUP #3 |
|---|
| Soft Rot |
| Acremonium strictum |
| Chaetomium globosum |
| Graphium rubrum |

The exposed samples were incubated for thirty days under conditions of 90% relative humidity and 32° C. temperature to promote fungal growth. After incubation the degree of fungal attack and decay to each sample was measured in square millimeters. The measurements were converted to express the percentage of wood surface area protected. The results are shown in Table 1. The preservative effectiveness for each composition shown in Table 1 is an average of ten measurements.

As seen from the data presented in said table, the wood preservative compositions of the present invention exert an unexpectedly increased wood preservative effect. More specifically, the compositions provided substantially improved resistance to fungi producing stain, mold, mildew, and soft rot while providing effective resistance to brown rot and white rot. The use of combinations of DDAC and IPBC are more effective than the use of either compound alone at the same concentration of preservative.

TABLE 1

| Wood Preservation Compositions Concentration of Active Ingredients | | | Average Preservative Effectiveness Against Six Economic Classes of Wood Damaging Fungi | | |
|---|---|---|---|---|---|
| | | | (Group #1) | (Group #2) | (Group #3) |
| Didecyldimethyl Ammonium Chloride | 3-Iodo-2-propynyl Butyl Carbamate | Total | Molds, Mildews and Stain fungi | Soft Rot Fungi | Brown and White Rot Decay Fungi |
| - Percent by Weight - | | | - Percent of Wood Surface Area Protected - | | |
| 0.2500 | 0.2500 | 0.5000 | 99a | 98a | 100a |
| 0.1250 | 0.1250 | 0.2500 | 61b | 65b | 100a |
| 0.0625 | 0.0625 | 0.1250 | 45c | 43c | 100a |
| 0 | 0.5000 | 0.5000 | 53bc | 60b | 100a |
| 0 | 0.2500 | 0.2500 | 26d | 32d | 100a |
| 0 | 0.1250 | 0.1250 | 20c | 25e | 90b |
| 0.5000 | 0 | 0.5000 | 7f | 0f | 90b |
| 0.2500 | 0 | 0.2500 | 4fg | 0f | 40c |
| 0.1250 | 0 | 0.1250 | 0g | 0f | 3d |
| 0 | 0 | 0 | 0g | 0f | 0d |

Within a column, means followed by the same letter are not significantly different at an 0.05 error rate of probability as determined by the Student t-test assuming unequal population variances.

EXAMPLE 2

Samples of pine wood (19×19×457 mm) were pressure treated with DDAC alone, IPBC alone, and a mixture of DDAC and IPBC. The samples were evaluated according to a standard wood preservative field test (ASTM D1758-74) with the fungi of Example 1 except Serpula lacrimans was not present. To obtain substantially equal wood preservative performance, which was measured after six months of exposure, the following concentrations of the respective preservatives were needed.

TABLE 2

| | Kilograms of Preservative per Cubic Meter of Wood Required for Protection | | |
|---|---|---|---|
| | IPBC | DDAC | DDAC and IPBC |
| Molds, Stain | 12.80 | 12.80 | 5.73    .67 |

As seen from the data presented in Table 2, the use of DDAC in admixture with IPBC is generally more effective against molds and stain at much lower concentrations than either compound used alone.

EXAMPLE 3

In order to obtain additional confirmation of the effectiveness of the compositions of the present invention in resisting wood staining additional tests were performed. More specifically, bioassay testing was carried out to demonstrate the synergistic effect of the use of the combination of DDAC and IPBC as contrasted with the use of other compounds individually.

EXAMPLE 4

In order to verify the effectiveness of other quaternary ammonium compounds the tests of Example 1 were repeated employing different quaternary ammonium compounds. In one series of tests the quaternary ammonium compound in the NP-1 (DDAC) was replaced by comparable concentrations of tri-methyl-coco-ammonium chloride and this formulation was designated "NP-50". The specific material employed was Arquad C-50, which contains 50% by weight tri-methyl-coco-ammonium chloride. In another series of tests dimethyl-di-coco-ammonium chloride was employed in comparable concentrations to the DDAC in NP-1. The specific material employed was Arquad 2C-75 which is 75% dimethyl-di-coco-ammonium chloride This composition was designated NP-50. In these tests the wood wafers were exposed to Diplodia gossypina, a common sapstain organism, as well as Aspergillus sp., Aureobasidium pullulans and Trichoderma viride all blended in equal parts. The NP-1 and untreated wafers were employed as controls. Unsterile conditions were followed in preparing the glass incubation plates. The results of this test are shown in Table 4.

TABLE 4

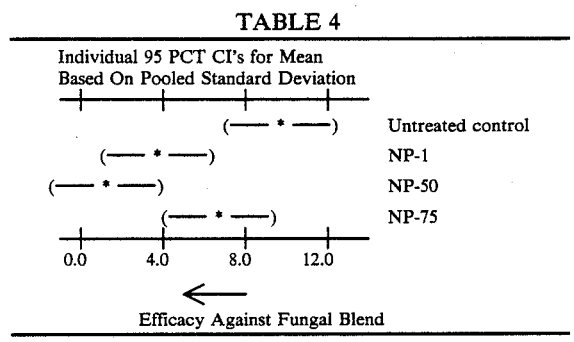

These tests show that the NP-50 and NP-75 formulations provide effective resistance to staining and the other organisms tested.

In conducting the tests a recognized bioassay screening procedure known as the Green Wood K-200 Screening Test was employed to evaluate antisapstain properties. The test procedure employed was as follows:

Candidate preservatives for antisapstain control can be tested using this test method. Samples are prepared as follows:

1. Samples are from Red Pine branches approximately 10 mm in diameter after bark has been removed, cut into 2-4 mm thickness. Several branches can be collected at one time and frozen to ensure freshness at time of test.

2. Samples are treated (30 second dip) in the candidate preservative formulation and then allowed to air dry for one hour. 3. Samples are then put in test. Samples are not sterilized.

In general, from ten to twenty replicates (samples should be used for each treatment (candidate preservative). Also, an untreated control should be used in each test (and dish) to evaluate the viability of each inoculum.

1. Preparation of Cultures
   a. Pure or group cultures are propagated at least four days in advance on a 7 cm filter paper soaked with 3 ml nutrient solution in a test tube.
   b. After growth covers the filter paper, 15 ml of sterile distilled water is added to the tube. Macerate until sample is homogenized. If group cultures are being used all samples should be mixed together in a sterile container with lid.

b 2. Preparation Of Test Chamber
   a. The chamber is a petri dish (glass or polycarbonate) with a connecting duct to a water reservoir and a lid with an 0.2 mm micropore vapor port.
   b. Tape the reservoir to the petri dish with heat resistant tape. Then fill the reservoir with distilled water and insert a piece of cellulose sponge into the reservoir duct.
   c. Sterilize these dishes in autoclave for 45 minutes at 121° C.
   d. Place adequate number of ashless 7 cm filter papers in container of nutrient solution. Sterilize in autoclave for 45 minutes at 121° C.
   e. Add to the dish three pieces of ashless 7 cm filter paper soaked in nutrient solution. Make sure that the filter paper and sponge make contact and that the filter paper is centered in the dish.

3. Test Completion
   a. Add the samples to the test chamber. The samples should be placed out of contact with each other and may be arranged in a circular pattern within the chamber. The samples do not sit on the filter paper, but they do overlap the paper by a few millimeters.

b Culture inoculum, 1.0 ml deuteromycete fungi blend, is added to the center of the filter paper.
   c. Incubate the dishes at 26° –32° C. and 70%–90% relative humidity.

4. Evaluation
   a. At five and fifteen days evaluate the samples. Evaluations are made visually using a scale from −10 to 10. Minus ten (−10) indicates an inhibitory zone of 10 mm around the sample. Zero (0) indicates no inhibitory zone, but the sample is not infected. Ten (10) indicates a sample covered with mycellium.

Analysis of Results

Evaluations are converted from the scale (−10 to 10)to express percentage of wood surface area protected using the following equation: [(Visual Evaluation)−10]×(−10)=Percentage of Wood Surface Area Protected For example:

[(0)−10]×(−10)=100% of wood surface area protected

After conversion, one way analyses of variance and Student's t-Tests are used to test for treatment differences at a determined error rate of probability (i.e., 0.05).

In these tests (a) 81% by weight of Bardac 2280, a germicidally active quaternary ammonium compound marketed by Lonza, Inc. and (b) 19% by weight of Troysan Polyphase AF-1, a fungicide marketed by Troy Chemical Corporation were employed. Bardac 2280 is 80% by weight didecyldimethyl ammonium chloride (DDAC) and Troysan Polyphase contains 40% by weight 3-iodo-2-propynyl butyl carbamate (IPBC) as its active material.

The effectiveness of each of the two components, DDAC and IPBC, and their combination, NP-1, in providing protection to wood was evaluated by the Green Wood K-200 procedure. Red pine samples treated with one of three test solutions were exposed to the common fungal staining organism, *Diplodia gossypina*. Ten replicates were included in the study. The experiment was run under unsterile conditions. Neither the red pine wafers nor the glass incubation plates were sterilized prior to use. The surface protection each treatment provided to the red pine samples was evaluated after 15 days of exposure and the experiment was then terminated. When the three test solutions were prepared, the total number of moles of active ingredients was kept constant. The concentration of actives in a 100:1 dilution of the compound of this invention ("NP-1") was used as the standard when making the other two solutions. NP-1 at a 100:1 dilution contains 0.00413 moles of active ingredients. Therefore, the two other test solutions which represent the individual components of NP-1 contained either 0.00413 moles of DDAC or 0.00413 moles of IPBC.

When the test specimens were evaluated after 15 days of exposure in the Green Wood K-200 series, it was observed that the untreated wafers had been overtaken by the Diplodia organism. The DDAC treated wafers demonstrated similar results, showing substantial attack. Some protection was provided by the IPBC treatment, as the growth on these wafers was not as severe as that on the untreated samples. However, statistical analysis defined the protection provided by the IPBC alone to be equal to that provided by the DDAC alone. In this experiment composition of the present invention ("NP-1") demonstrated the greatest efficacy against the common sapstain organism, allowing little or no growth on the treated wafers.

The scale illustrated in Table 5 shows the degree of inhibition of staining of the wood samples with the lowest values indicating the best resistance to staining. Table 5 shows individual 95% confidence intervals for mean based on pooled standard deviation. It will be readily appreciated that the stain inhibition properties of NP-1 were markedly superior to those of the untreated sample, the DDAC alone, and the IPBC alone. Further, the DDAC and IPBC were much closer in performance to the untreated control than to the NP-1. These tests clearly demonstrate the synergistic effect produced by the NP-1. The combination of DDAC and IPBC provided significantly greater protection against a common sapstain organism than equimolar treatments of either of the two components taken alone.

TABLE 5

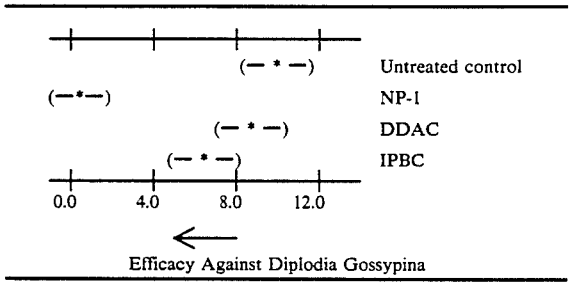

Efficacy Against Diplodia Gossypina

EXAMPLE 5

The composition of the invention (NP-1) as employed in Example 3 may be prepared in the following manner.

An open vessel equipped with agitation is charged with 19 parts by weight of Troysan Polyphase AF-1, a liquid consisting of 40% by weight of 3-iodo-2-propynyl butyl carbamate (IPBC). To this is added under gentle agitation 81 parts by weight of Bardac 2280, a solution of 80% by weight of didecyldimethyl ammonium chloride (DDAC). The resulting mixture is a stable microemulsion of IPBC in DDAC, 100 parts by weight of NP-1.

The compositions of the present invention may be applied to the wood to be protected by means well known to those skilled in the art. The material may be applied to wood, for example, by dipping, brushing, spraying or pressure impregnation. The concentrate is generally diluted to working solution strength by addition of water. The concentrate is diluted from about 15 to 300 times with water depending on the severity of the environmental conditions and the length of protection desired. If desired, buffers, water repellents and other additives may be added to the treating solution. Historical buffers or anticorrosives, such as borax or soda ash may be added as well as iron chelating compounds such as phosphoric acid and phosphonic acid. Insecticides as well as dyes, pigments, resins and water repellents may be added, if desired.

In general, for control of sapstain in green lumber the preferred methods of application are by dipping or spraying.

For lumber which will be utilized in more severe environments, pressure treatment is a preferred method of application.

It will be appreciated that the present invention has provided an improved wood preservative composition for wood. The composition provides enhanced sapstain resistance while also providing effective resistance to mold, mildew, soft rot, brown rot and white rot. All of this is accomplished by employing a synergistic wood preservative composition comprising 3-iodo-2-propynyl butyl carbamate and a material selected from the group consisting of didecyldimethyl ammonium chloride, tri-methyl-coco-ammonium chloride and dimethyl-di-coco-ammonium chloride.

Whereas particular embodiments of the invention have been described herein, for purposes of illustration, it will be evident to those skilled in the art that numerous variations of the details may be made without departing from the invention as defined in the appended claims.

WHAT IS CLAIMED:

1. A synergistic wood preservative composition comprising quaternary ammonium compound and 3-iodo- 2propynyl butyl carbamate and having the property of providing stain resistance to wood.

2. The composition of claim 1, including said quaternary ammonium compound being selected from the group consisting of didecyldimethyl ammonium chloride, tri-methyl-coco-ammonium chloride and dimethyl-di-coco-ammonium chloride.

3. The composition of claim 2, wherein a water solution of said quaternary ammonium compound is present with an organic solvent solution of 3-iodo-2-propynyl butyl carbamate to create an emulsion.

4. The composition of claim 2, wherein the composition contains from about 4–20 parts per weight of said quaternary ammonium compound per 1 part per weight of 3-iodo-2-propynyl butyl carbamate.

5. The composition of claim 2, wherein said quaternary ammonium compound is didecyldimethyl ammonium chloride.

6. The composition of claim 2, wherein said quaternary ammonium compound is tri-methyl-coco-ammonium chloride.

7. The composition of claim 2, wherein said quaternary ammonium compound is dimethyl-di-coco-ammonium chloride.

8. The composition of claim 1, wherein the composition contains from about 1–80 parts per weight of said quaternary ammonium compound per about 1–10 parts per weight of 3-iodo-2-propynyl butyl carbamate.

* * * * *